(12) United States Patent
Ham et al.

(10) Patent No.: US 11,058,736 B2
(45) Date of Patent: Jul. 13, 2021

(54) **METHOD OF TREATING DRY EYE SYNDROME USING PHARMACEUTICAL COMPOSITION HAVING EXTRACT OF *TERMINALIA CHEBULA* OR FRACTION THEREOF**

(71) Applicant: KOREA INSTITUTE OF SCIENCE AND TECHNOLOGY, Seoul (KR)

(72) Inventors: Jungyeob Ham, Gangneung-si (KR);
Jin-Chul Kim, Gangneung-si (KR);
Chang Geon Kim, Gangneung-si (KR);
Bong Geun Song, Gangneung-si (KR);
Taejung Kim, Gangneung-si (KR);
Pilju Choi, Gangneung-si (KR);
Seon-Jun Choi, Gangneung-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/549,767

(22) Filed: Aug. 23, 2019

(65) Prior Publication Data
US 2020/0061137 A1 Feb. 27, 2020

(30) Foreign Application Priority Data
Aug. 24, 2018 (KR) ........................ 10-2018-0099427

(51) Int. Cl.
*A61K 36/185* (2006.01)
*A61P 27/04* (2006.01)
*A61K 9/00* (2006.01)

(52) U.S. Cl.
CPC ............ *A61K 36/185* (2013.01); *A61P 27/04* (2018.01); *A61K 9/0048* (2013.01); *A61K 9/0053* (2013.01)

(58) Field of Classification Search
None
See application file for complete search history.

(56) References Cited

U.S. PATENT DOCUMENTS 10,799,447 B2 * 10/2020 Rynerson ............. A61K 31/047

FOREIGN PATENT DOCUMENTS

| CN | 104983905 | * | 6/2015 | |
|----|-----------|---|--------|---|
| CN | 105012404 | * | 11/2015 | |
| JP | 2003-238432 A | | 8/2003 | |
| KR | 10-2004-0035364 A | | 4/2004 | |
| WO | WO-2006003383 A1 | * | 1/2006 | ............. A61K 36/54 |

OTHER PUBLICATIONS

Gupta, P. Biological and Pharmacological Properties of *T. chebula* (Haritaki). Int. J of Pharmacy and Pharmaceutical Sciences 4(Suppl 3)62-68, Jun. 2012. (Year: 2012).*
Biswas N. et al. Comparative Randomised Controlled Clinical Trial of an Herbal Eye Drop with Artificial Tearand Placebo . . . J of the Indian Medical Association 101(3)208-209, 212, Mar. 2003. (Year: 2003).*
Pooja V. K. et al. A Review on Ayurvedic Medicinal Plants for Eye Disorders from Ancient to Modern Era. Int J of Pharmaceutical Sciences and Research 5(12)5088-5096, 2014. (Year: 2014).*
Korean Office Action, dated Dec. 6, 2019, for Koean Application No. 10-2018-0099427.

* cited by examiner

*Primary Examiner* — Ralph J Gitomer
(74) *Attorney, Agent, or Firm* — Birch, Stewart, Kolasch & Birch, LLP

(57) ABSTRACT

Provided are a pharmaceutical composition for preventing or treating dry eye syndrome, including an extract of *Terminalia chebula* or a fraction thereof as an active ingredient, and a method of preventing or treating dry eye syndrome in an individual.

4 Claims, 12 Drawing Sheets
Specification includes a Sequence Listing.

METHOD OF TREATING DRY EYE SYNDROME USING PHARMACEUTICAL COMPOSITION HAVING EXTRACT OF *TERMINALIA CHEBULA* OR FRACTION THEREOF

CROSS-REFERENCE TO RELATED APPLICATION

This application claims the benefit of Korean Patent Application No. 10-2018-0099427, filed on Aug. 24, 2018, in the Korean Intellectual Property Office, the disclosure of which is incorporated herein in its entirety by reference.

REFERENCE TO SEQUENCE LISTING SUBMITTED VIA EFS-WEB

This application includes an electronically submitted sequence listing in .txt format. The .txt file contains a sequence listing entitled "2019-11-04_SEQ-LISTING_1183-0136PUS1_ST25.txt" created on Oct. 30, 2019 and is 2,729 bytes in size. The sequence listing contained in this .txt file is part of the specification and is hereby incorporated by reference herein in its entirety.

BACKGROUND

1. Field

One or more embodiments relate to a pharmaceutical composition for preventing or treating dry eye syndrome including an extract of *Terminalia chebula* or a fraction thereof and a method of preventing or treating dry eye syndrome in an individual.

2. Description of Related Art

Dry eye syndrome (DES), an ocular disease also known as keratoconjunctivitis sicca, is a multifactorial disorder of tears and the tear film, and common symptoms thereof include irritation, foreign body sensation, light sensitivity, and itching. Although dry eye syndrome refers to an inflammatory disease of the eyes, the pathogenesis thereof has not been fully identified yet. However, it has been reported that inflammation, such as inflammatory cell infiltration, increases in the expression level of immune-activating molecules and adhesive molecules, responses of T helper cell type 1 (Th1) and T helper cell type 17 (Th17), and abnormal changes of inflammatory cytokines, which plays an important role in dry eye syndrome.

In general, artificial tears have been used to treat dry eye syndrome. Although artificial tears may control mild symptoms, effects thereof are temporary. Anti-inflammatory agents such as corticosteroids and cyclosporine have been used to treat dry eye syndrome. However, prolonged use thereof may increase the risk of developing side effects such as glaucoma and cataracts or cause redness or irritation in eyeballs. Thus, there are few known long-term treatments or functional foods for dry eye syndrome.

Meanwhile, *Terminalia* fruit is a dried ripe fruit of *Terminalia chebula* Retz. which is a member of family Combretaceae. Korean Patent Laid-open Publication No. 10-2004-0035364 discloses a whitening composition containing an extract of *Terminalia chebula*.

As a result of extensive research into a composition for preventing and treating dry eye syndrome derived from natural products, the present inventors have found that an extract of *Terminalia chebula* or a fraction thereof is able to treat and alleviate dry eye syndrome by increasing the amount of tear secretion and inhibiting corneal morphological changes and inflammation, thereby completing the present disclosure.

SUMMARY

One or more embodiments include a pharmaceutical composition for preventing or treating dry eye syndrome, including an extract of *Terminalia chebula* or a fraction thereof as an active ingredient.

One or more embodiments include a method of treating dry eye syndrome in an individual, including administering the pharmaceutical composition to the individual in an amount effective to prevent or treat dry eye syndrome.

Additional aspects will be set forth in part in the description which follows and, in part, will be apparent from the description, or may be learned by practice of the presented embodiments of the disclosure According to one or more embodiments, a pharmaceutical composition for preventing or treating dry eye syndrome includes an extract of *Terminalia chebula* or a fraction thereof as an active ingredient.

As used herein, the term "dry eye syndrome" collectively refers to eye diseases having damaged ocular surfaces caused when eyes do not produce enough tears, when the tears evaporate too quickly, or when tear components are not balanced.

The extract of *Terminalia chebula* having the preventive and therapeutic activity of dry eye syndrome may be obtained from various organs of natural, hybrid, and variant plants thereof, e.g., not only roots, trunks, leaves, flowers, flesh and skin of fruits, but also, tissue cultures thereof, and preferably from fruits of *Terminalia chebula*.

As used herein, the term "*Terminalia* fruit" refers to a fruit of *Terminalia chebula*, which is a tall tropical tree native to India, Myanmar, Malaysia, Sichuan, China, and the like, and a yellow dye called myrobalan may be extracted from fruit juices and the tree may be used for the manufacture of furniture. The fruit has a hard outer surface with a yellowish brown to brown color with gloss and has 5 to 6 vertical wrinkles with irregular wrinkles therebetween. In Korea and Japan, dried flesh of ripe fruits of *Terminalia chebula* Retzius from which seeds are removed has been used as a medicinal substance in a folk remedy. In addition to astringent action and anti-bacterial activity against dysentery bacilli and staphylococci, this medicinal substance has been used to stop diarrhea and cough in the folk remedy. Also, this medicinal substance is used to treat diarrhea, dysentery, cough, and the like and also has been used to treat various disease such as enterorrhagia, anal prolapse, metrorrhagia, hoarse voice, leucorrhea, ganacratia, and frequent urination in the traditional medicine in Asian countries as well as Korea.

The extract of *Terminalia chebula* according to the present disclosure may be a solvent extract obtained by extracting with an extraction solvent, a fraction obtained by adding a fractionation solvent to the obtained extract, or a purified product obtained by performing chromatography on the fraction.

The extraction solvent may be water, an organic solvent, or any mixture thereof available in extraction of natural products. The extraction solvent may be water, a C1-C6 alcohol, or any mixture thereof, e.g., water or ethanol.

The extract of *Terminalia chebula* according to the present disclosure may be prepared according to any known method of preparing plant extracts. More particularly, preparation of the extract of *Terminalia chebula* may be performed using an extraction method including removing impurities from dried *Terminalia* fruit, pulverizing the dried fruit, adding an extraction solvent to the pulverized product, and conducting extraction. The extraction method using a solvent may be hot water extraction, cold immersion extraction, reflux cooling extraction, ultrosonication extraction, and preferably cold immersion extraction. The extract may be obtained by extracting an active ingredient from *Terminalia* fruit by incubating the *Terminalia* fruit in a solvent. The incubating may be performed at a reflux temperature of 4° C. to 100° C., 4° C. to 80° C., 4° C. to 60° C., 4° C. to 50° C., 4° C. to 40° C., 4° C. to 35° C., 4° C. to 30° C., 4° C. to 25° C., or at room temperature. The incubating may be performed for a time sufficient to extract the active ingredient in the solvent. The incubating time may be 1 hour to 2 weeks, 1 hour to 1 week, 1 hour to 5 days, 1 hour to 3 days, 12 hours to 5 days, 12 hours to 3 days, 12 hours to 2 days, 24 hours to 5 days, or 24 hours to 3 days.

As used herein, the term "fraction" refers to a resultant obtained by performing fractionation to isolate a particular component or particular component group from a mixture of various components.

Also, preparation of a fraction of the extract may be conducted by adding a fractionation solvents to the extract obtained according to the extraction method and performing fractionation according to polarity of the fractionation solvent. The obtaining of the fraction may be performed by a separation method or a fractionation method via layer separation. More particularly, after adding a fractionation solvent to the extract, for example, sequentially adding fractionation solvents such as hexane, chloroform, ethylacetate, butanol, and water thereto, a hexane fraction, a chloroform fraction, an ethylacetate fraction, a butanol fraction, and a water fraction whose layers are separated may be obtained therefrom.

The fractionations method via layer separation may be a method of obtaining fractions by sequentially adding solvents to the extract according to degrees of non-polarity of the solvents, and obtaining each of the fractions contained in layers separated at each application, e.g., a method of sequentially obtaining a hexane fraction by adding hexane to an aqueous ethanol solution of the extract followed by fractionation of a separated hexane layer; a chloroform fraction by adding chloroform to a remaining water layer after the hexane fraction is separated followed by fractionation of a separated chloroform layer; an ethylacetate fraction by adding ethylacetate to a remaining water layer after the chloroform fraction is separated followed by fractionation of a separated ethylacetate layer; a butanol fraction by adding butanol to a remaining water layer after the ethylacetate fraction is separated followed by fractionation of a separated butanol layer, and a water fraction obtained after the butanol fraction is separated.

In the present disclosure, after obtaining an ethanol extract of *Terminalia* fruit by a method according to Example 1 is suspended in distilled water, the above-described fractions of the *Terminalia* fruits were obtained by systematical fractionation sequentially using hexane, chloroform, ethylacetate, butanol, and water, and thus a 10% hexane fraction and a hexane washing fraction were obtained via C18 reversed-phase chromatography.

The chromatography for purifying the fractions may be performed by various methods such as silica gel column chromatography, thin layer chromatography (TLC) or high-performance liquid chromatography (HPLC).

As used herein, the term "preventing" refers to all actions intended to inhibit or delay symptoms associated with dry eye syndrome to be close to a state of a normal control group by administering the composition including an extract of *Terminalia chebula* or a fraction thereof according to present disclosure.

As used herein, the term "treating" refers to all activities that alleviate or beneficially change symptoms associated with dry eye syndrome to be close to a state of a normal control group by administering the composition including an extract of *Terminalia chebula* or a fraction thereof according to present disclosure.

In the present disclosure, the composition may increase the amounts of tear secretion or inhibit thickness changes and inflammation in a cornea. The morphological changes in a cornea are caused by a decrease in a surface thickness of a cornea to be smaller than that of a normal control group due to overdrying of tears, and the inflammation is caused by an increase in the number of inflammatory cells due to inflammatory responses thereof, and the composition according to the present disclosure may alleviate morphological changes and inflammation in the cornea.

In the present disclosure, the composition may inhibit morphological changes and inflammation in lacrimal glands. The morphological changes in a lacrimal gland are caused by an increase in a gap between cells because sizes of acinar cells are reduced to be smaller than those of a normal control group due to overdrying of tears and the inflammation may be caused by an increase in the number of inflammatory cells due to inflammatory responses thereof, and the composition according to the present disclosure may alleviate morphological changes and inflammation in the lacrimal gland.

According to an embodiment of the present disclosure, it was confirmed that the amounts of tear secretion significantly increased and corneal damage areas decreased in most of the fraction-treated groups at 14 days after administering thereto a crude the *Terminalia* fruit extract and the fractions thereof obtained using hexane, ethylacetate, chloroform, butanol, and water as solvents, when compared with a dry eye syndrome-induced group. It was identified that these results were similar to that of the normal control group without dry eye syndrome.

According to another embodiment, it was confirmed that thickness changes and inflammation, which are observed in the dry eye syndrome-induced group, were significantly inhibited in corneas by administering the crude the *Terminalia* fruit extract and the fractions thereof obtained using hexane, ethylacetate, chloroform, butanol, and water as solvents. It was identified that these results were similar to that of the normal control group without dry eye syndrome.

According to another embodiment, it was confirmed that morphological changes and inflammation, which are observed in the dry eye syndrome-induced group, were significantly inhibited in lacrimal glands by administering the crude the *Terminalia* fruit extract and the fractions thereof obtained using hexane, ethylacetate, chloroform, butanol, and water as solvents. It was identified that these results were similar to that of the normal control group without dry eye syndrome.

According to an embodiment of the present disclosure, it was confirmed that the amounts of tear secretion significantly increased and corneal damage areas decreased in most of the fraction-treated groups at 14 days after administering fractions obtained from the ethanol extract of *Terminalia* fruit by treating with hexane, 10% hexane, and hexane washing, when compared with a dry eye syndrome-induced group. It was identified that these results were similar to that of the normal control group without dry eye syndrome.

According to an embodiment of the present disclosure, it was confirmed that thickness changes and inflammation, which are observed in the dry eye syndrome-induced group, were significantly inhibited in corneas by administering the fractions of *Terminalia* fruit obtained using hexane as a solvent (hexane, 10% hexane, and hexane washing). It was identified that these results were similar to that of the normal control group without dry eye syndrome.

According to an embodiment of the present disclosure, it was confirmed that morphological changes and inflammation, which are observed in the dry eye syndrome-induced group, were significantly inhibited in lacrimal glands by administering the fractions of *Terminalia* fruit obtained using hexane as a solvent (hexane, 10% hexane, and hexane washing). It was identified that these results were similar to that of the normal control group without dry eye syndrome.

Thus, based on the above results, it was confirmed that the extract of *Terminalia chebula* or the fraction thereof has a therapeutic effect on dry eye syndrome.

As used herein, the term "pharmaceutical composition" refers to a composition prepared for the purpose of preventing or treating a disease and may be formulated in various forms according to any method commonly used in the art. For example, the pharmaceutical composition may be formulated into an eye drop, a cream, an ointment, a gel, or a lotion and also be formulated into a formulation for external use, a suppository, and a sterile injection solution. Particularly, the composition may be used in any formulation suitable for oral administration, e.g., powders, granules, tablets, capsules, suspensions, emulsions, and syrups.

A dose of the pharmaceutical composition according to the present disclosure may be determined by one of ordinary skill in the art in consideration of factors well known in the medical fields such as a purpose of use, severity of disease, age, weight, health status, gender, and sensitivity to drug of a patient, a period and a route of administration, or a type of a substance used as an active ingredient.

The composition may include the extract of *Terminalia chebula* or a fraction thereof as a single active ingredient. That is, the composition does not include any other single active ingredient than the extract of *Terminalia chebula* or the fraction thereof.

According to one or more embodiments, a method of treating dry eye syndrome in an individual includes administering the pharmaceutical composition to the individual in an effective amount for preventing or treating dry eye syndrome.

The individual may be a mammal. The mammal may be a human being, a dog, a cat, a cow, a goat, or a pig.

The administration may be performed via any conventional route of administration to deliver the composition to a target tissue. For example, the composition may be administered according to a desired purpose via a route of administration such as eye-drop administration, intraperitoneal administration, intravenous administration, intramuscular administration, subcutaneous administration, intradermal administration, transdermal patch administration, oral administration, intranasal administration, intrapulmonary administration, and rectal administration, particularly, via eye-drop administration.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
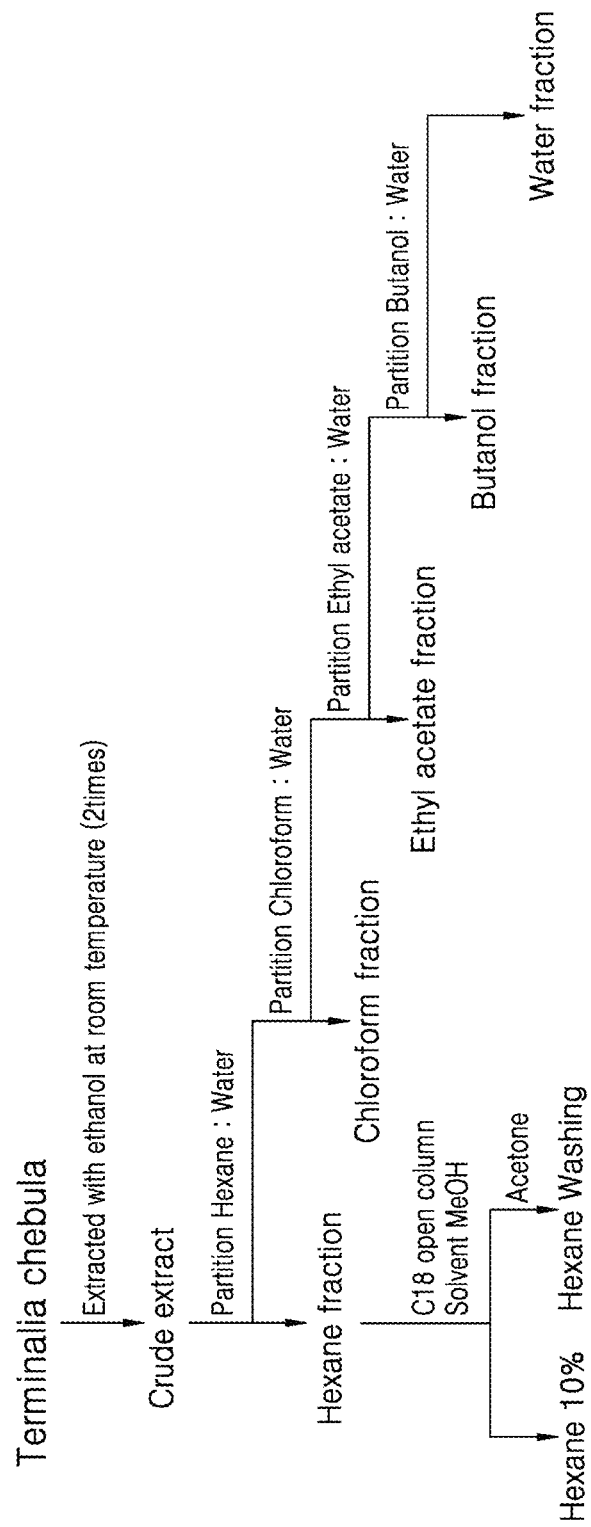
FIG. 1 is a schematic diagram illustrating systematic fractionation of an ethanol extract of *Terminalia* fruit sequentially using hexane, chloroform, ethyl acetate, and butanol, and separation of the hexane fraction using C18 reversed-phase chromatography.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Example 1: Preparation of Extract of *Terminalia chebula* and Fraction Thereof

In this example, 600 g of *Terminalia chebula* was subjected to extraction with ethanol and then subjected to fractionation sequentially using hexane, chloroform, ethylacetate, and butanol as solvents to obtain 870 mg, 1.57 g, 9 g, and 20 g of solvent fractions thereof, respectively, and 82 g of an aqueous solution layer was obtained. Among them, a hexane fraction was subjected to column chromatography using C18 reversed-phase silica gel as a stationary phase and methanol as a mobile phase to obtain two fractions therefrom.

1. Preparation of Ethanol Extract

Seeds were removed from ripe fruits of *Terminalia chebula*, and flesh of the fruits was dried. 600 g of the dried flesh was immersed in 2 L of 100% ethanol and maintained at room temperature for 24 hours, and this process was repeated twice. A filtrate obtained by filtering the solution using filter paper was distilled under a reduced pressure at 35° C. to obtain 121 g of a crude extract 121 g (hereinafter, referred to as "ethanol extract").

FIG. 1 is a diagram illustrating a process of preparing an extract of *Terminalia chebula* and fractions thereof.

2. Preparation of Fraction (1) Fraction of Hexane 121 g of the crude extract of *Terminalia* fruit obtained in section 1 above was dissolved in 800 mL of water, and the solution was mixed with 800 mL of hexane. The mixture was maintained at room temperature for 24 hours and a hexane layer was separated therefrom. This process was repeated three times and a hexane layer obtained therefrom was distilled under a reduced pressure to obtain 870 mg of an extract of the hexane layer (hereinafter, referred to as 'hexane fraction').

(2) Fraction of Chloroform

A remaining water layer after obtaining the hexane fraction in section (1) above was mixed with 800 mL of chloroform and the mixture was maintained at room temperature for 24 hours, and then a chloroform layer was separated therefrom. This process was repeated three times and a chloroform layer obtained therefrom was distilled under a reduced pressure to obtain 1.57 g of an extract of the chloroform layer (hereinafter, referred to as 'chloroform fraction').

(3) Fraction of Ethylacetate

A remaining water layer after obtaining the chloroform fraction in section (2) above was mixed with 800 mL of ethylacetate and the mixture was maintained at room temperature for 24 hours, and then an ethylacetate layer was separated therefrom. This process was repeated three times and an ethylacetate layer obtained therefrom was distilled under a reduced pressure to obtain 9 g of an extract of the ethylacetate layer (hereinafter, referred to as 'ethylacetate fraction').

(4) Fraction of Butanol

A remaining water layer after obtaining the ethylacetate fraction in section (3) above was mixed with 800 mL of butanol and the mixture was maintained at room temperature for 24 hours, and then a butanol layer was separated therefrom. This process was repeated twice and a butanol layer obtained therefrom was distilled under a reduced pressure to obtain 20 g of an extract of the butanol layer (hereinafter, referred to as 'butanol fraction').

(5) Fraction of Water

A remaining water layer after separating the butanol layer in section (4) above was distilled under a reduced pressure to obtain 82 g of a water layer extract (hereinafter, referred to as 'water fraction').

(6) Separation of Hexane Fraction by C18 Reversed-Phase Silica Gel 800 mg out of 870 mg of the hexane fraction of the crud extract of *Terminalia* fruit obtained in section 1 above was subjected to column chromatography using C18 reversed-phase silica gel as a stationary phase and methanol as a mobile phase to obtain two fractions therefrom.

The two fractions were obtained by filling a C18 resin in a glass column (diameter of 9.3 cm×length of 8.0 cm) and using methanol as a solvent. Hereinafter, the two fractions will be referred to as 'Hexane 10%' and 'Hexane Washing'. 'Hexane 10%' indicates 87 mg a fraction obtained by distilling a fraction obtained by flowing a mixed solvent of 10% of methanol and 90% of water through the glass column filled with the C18 resin under a reduced pressure, and 'Hexane Washing' indicates 120 mg of a dry extract obtained by distilling a fraction obtained using 100% of acetone as an eluent.

Example 2: Evaluation of Effect Using Test Animal

1. Preparation of Dry Eye Syndrome Animal Model 6-week-old male Balb/c were purchased mice (Kangwon Life Science, Korea) and acclimated for one week, and then continuously maintained under drying conditions of a humidity of 35% for 14 days using a 24-hour dehumidifier to induce dry eye syndrome.

2. Animal Test Design

To identify the effects of fractions of *Terminalia* fruit on the dry eye syndrome induced by the dehumidifier, the test animals prepared section 1 above were used. Five individuals were randomly assigned to each of the groups for tests: a normal control group without any treatment (Con), a disease group in which dry eye syndrome is induced using the dehumidifier according to the method of section 1 above (DE), a crude group of an ethanol extract of *Terminalia* fruit, and fraction groups of the ethanol extract including a hexane group, an ethylacetate group, a chloroform group, a butanol group, and a water group, i.e., one normal control group, one disease group, and six fraction-treated groups.

Also, the hexane group exhibiting the most effective improvement was subjected to fractionation into 5 groups including a hexane group, 10% hexane group, and a hexane washing group. A concentration of a drug containing a fraction of *Terminalia* fruit and administered to the fraction-treated group according to the present disclosure was set to 40 mg/kg, and a sterile physiological saline solution including 0.5% dimethyl sulfoxide (DMSO) was used as a vehicle to dissolve the fraction at the concentration. The drug was orally administered twice a day in the morning and evening using a Sonde to investigate availability as a health functional food, and the same dose of the vehicle was only administered to the normal control group and the disease group.

3. Measurement of Amount of Tear Secretion and Decreased Degree of Corneal Damage Area The effects of fractions of *Terminalia* fruit on amounts of tear secretion and decrease in corneal damage areas in the dry eye syndrome induced by the dehumidifier were identified. At 14 days after administering the drug, amounts of tears of the mice according to the animal test design of section 2 were measured by Schirmer's test and then decreases in corneal damage areas in eyes of the mice were identified by fluorescence staining.

Figure 2:
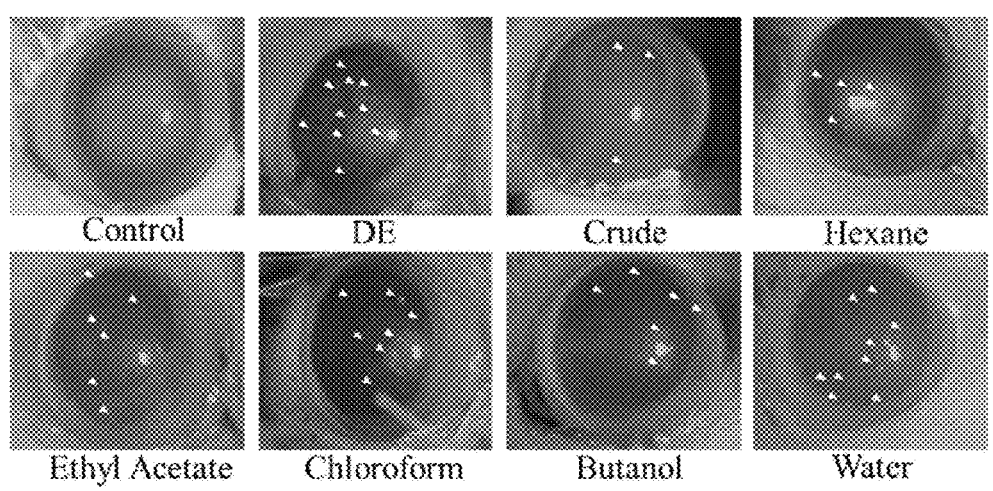
FIG. 2 shows photographs showing reduced corneal damage areas in mice according to the administration of fractions of *Terminalia* fruit.

FIG. 2 shows photographs showing reduced corneal damage areas in mice according to administration of fractions of *Terminalia* fruit. In FIG. 2, arrows indicate the degrees of corneal damage identified using a fluorescein dye. As shown in FIG. 2, in the crude group, the hexane group, the ethylacetate group, the chloroform group, and the butanol group, corneal damage areas decreased, compared with the DE group. These results are indicated as reduced number of the arrows in FIG. 2. Among them, the crude group and the hexane group exhibited less corneal damage areas than that of the DE group.

Figure 3:
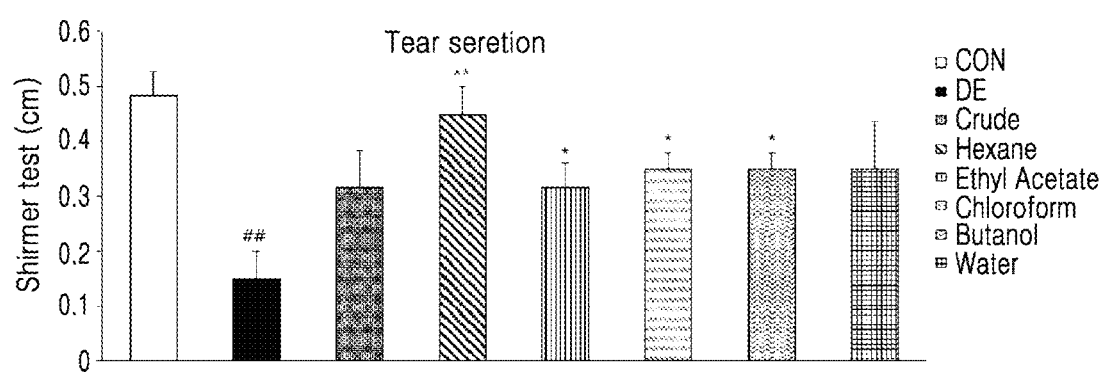
FIG. 3 is a graph illustrating changes in tear secretion levels in mice according to administration of fractions of *Terminalia* fruit (*: $p<0.05$ vs. Con; #: $p<0.05$ vs. DE)

FIG. 3 is a graph illustrating changes in tear secretion levels in mice according to administration of fractions of *Terminalia* fruit (*: $p<0.05$ vs. Con; #: $p<0.05$ vs. DE).

As shown in FIG. 3, the amounts of tear secretion of the crude group, the hexane group, the ethylacetate group, the chloroform group, and butanol group were greater than that of the DE group. Among them, the hexane group exhibited the greatest amount of tear secretion, compared to the DE group.

Figure 4:
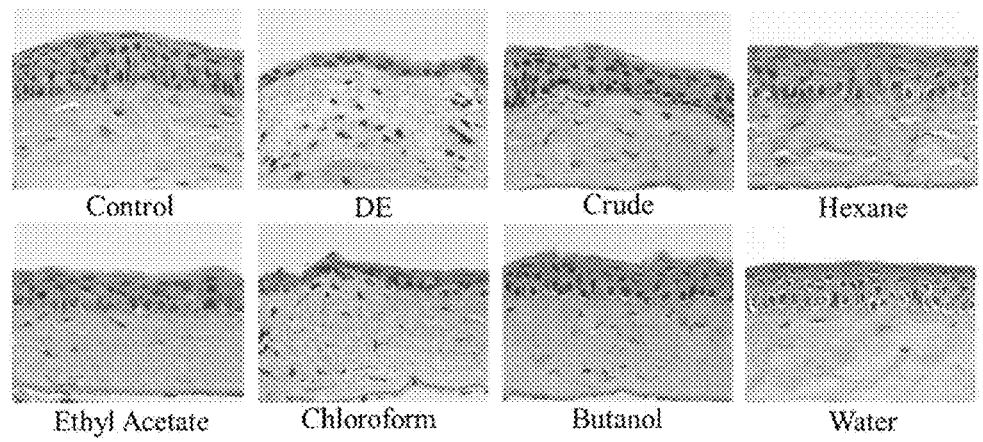
FIG. 4 shows photographs showing changes in corneal thickness in mice according to administration of fractions of *Terminalia* fruit.
Figure 4:
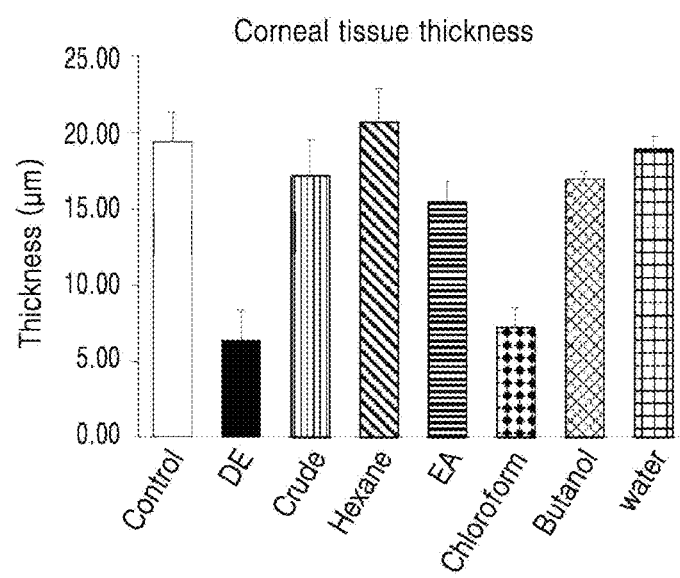

FIG. 4 shows photographs showing changes in corneal thickness in mice according to administration of the hexane fractions of *Terminalia* fruit. As shown in FIG. 4, decreases in thicknesses of corneas by inflammation caused by the dry eye syndrome were observed.

Figure 5:
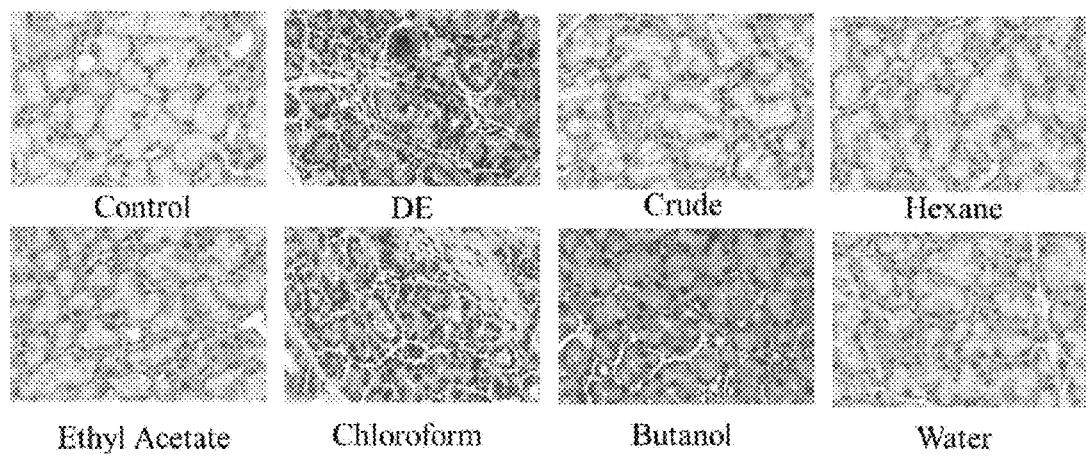
FIG. 5 shows photographs showing morphological changes of lacrimal glands in mice according to the administration of fractions of *Terminalia* fruit.
Figure 6:
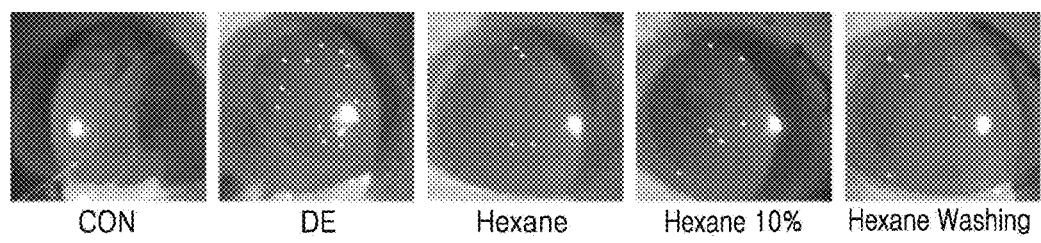
FIG. 6 shows photographs showing reduced corneal damage sites in mice according to the administration of hexane fractions of *Terminalia* fruit.

FIG. 5 is a graph illustrating changes in amounts of tear secretion in mice by administering hexane fractions of *Terminalia* fruit (*: $p<0.05$ vs. Con; #: $p<0.05$ vs. DE)

4. Measurement of Thickness of Cornea and Morphological Change in Lacrimal Gland The effects of fractions of *Terminalia* fruit on thicknesses of corneas and morphological changes in lacrimal glands in the dry eye syndrome induced by the dehumidifier were identified. Particularly, at 14 days after administering the drug, tissues of eyeballs and lacrimal glands of the mice prepared according to the animal test design in section 2 above were observed by H&E staining.

Figure 8:
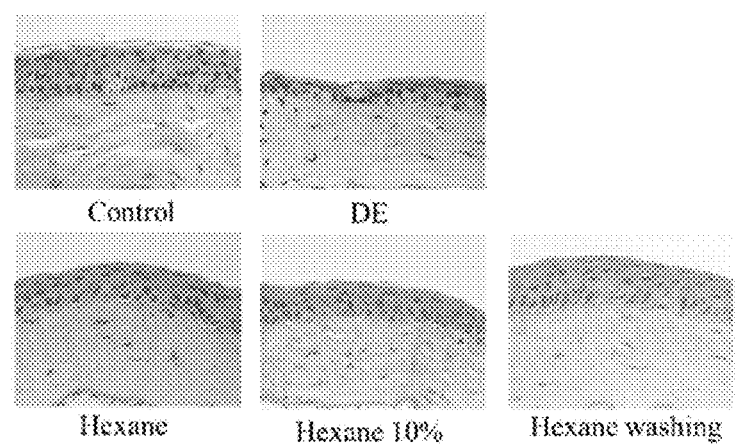
FIG. 8 shows photographs showing changes in corneal thickness in mice according to the administration of hexane fractions of *Terminalia* fruit.
Figure 8:
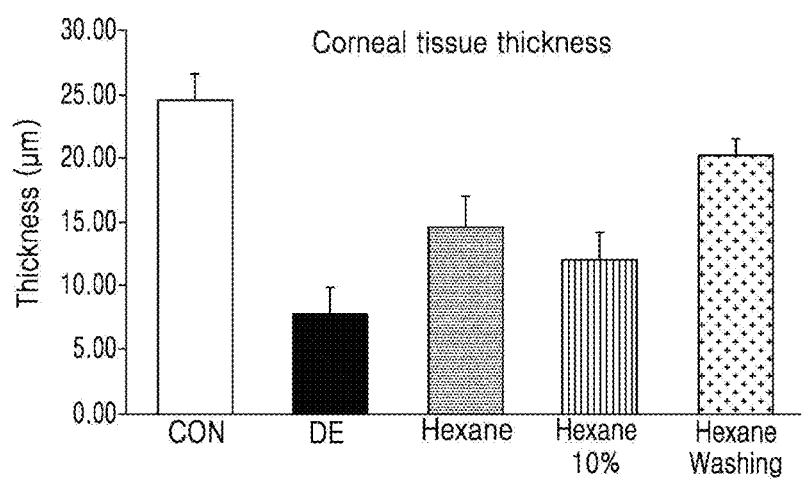

FIG. 8 shows photographs exhibiting changes in thickness of corneas of mice by administering hexane fractions of *Terminalia* fruit (left) and a graph illustrating measured thicknesses of the corneas (right). As shown in FIG. 8, the thicknesses increased in the crude group, the hexane group, the ethylacetate group, the chloroform group, the butanol group, and the water group, compared to the DE group. Among then, the hexane group exhibited the greatest thickness of the cornea. Thus, it was confirmed that the thickness of the corneas increased to be similar to that of the normal control group and the number of the inflammatory cells decreased and shrinkage of the acinar cells was reduced in the lacrimal glands in the groups treated with the extract and the fractions of the respective solvents.

Figure 7:
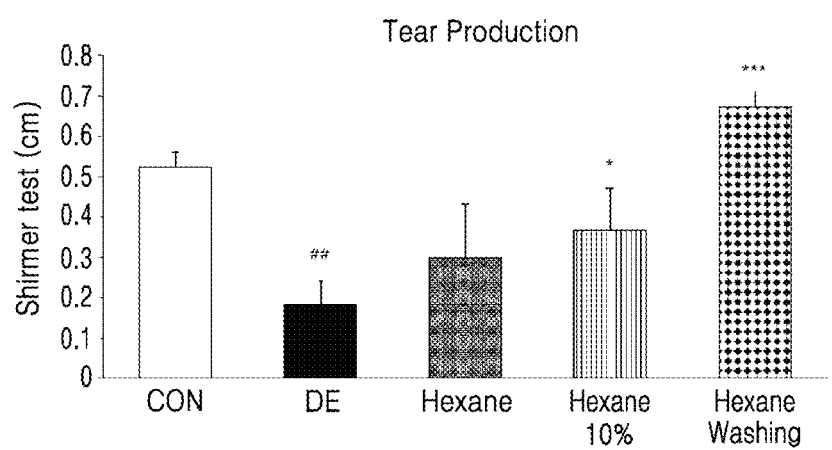
FIG. 7 is a graph illustrating changes in tear secretion levels in mice according to administration of hexane fractions of *Terminalia* fruit (*: $p<0.05$ vs. Con; #: $p<0.05$ vs. DE)

FIG. 7 is a graph illustrating changes in tear secretion levels in mice according to administration of fractions of *Terminalia* fruit. As shown in FIG. 7, increases in the amounts of tear secretion, which were decreased by the dry eye syndrome, were observed in the groups treated with hexane fractions.

FIG. 8 shows photographs showing changes in corneal thickness in mice according to administration hexane fractions of *Terminalia* fruit. As shown in FIG. 8, it was observed that the thicknesses of the cornea, which was decreased by inflammation caused by the dry eye syndrome, increased by the hexane fractions.

Figure 9:
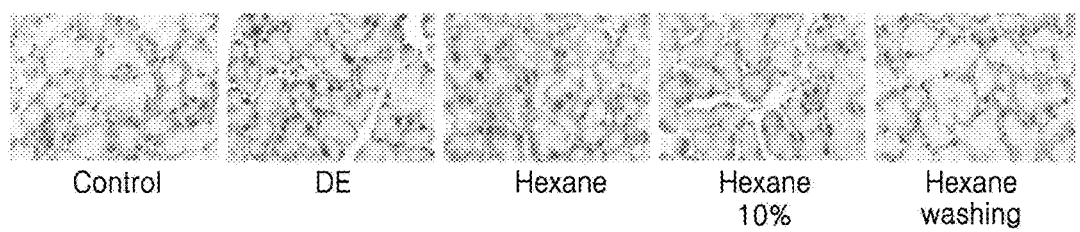
FIG. 9 shows photographs showing morphological changes of lacrimal glands in mice according to the administration of hexane fractions of *Terminalia* fruit.
Figure 10A:
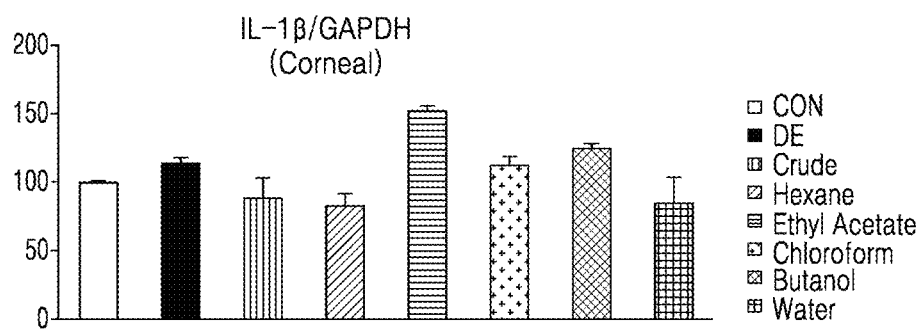
FIGS. 10A, 10B, 10C, and 10D are graphs illustrating expression of inflammatory cytokines in corneas of mice according to the administration of fractions of *Terminalia* fruit (*: $p<0.05$ vs. Con; #: $p<0.05$ vs. DE)
Figure 10B:
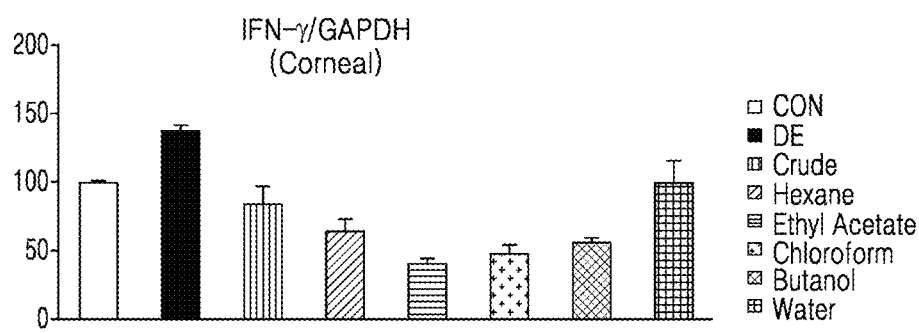
Figure 10C:
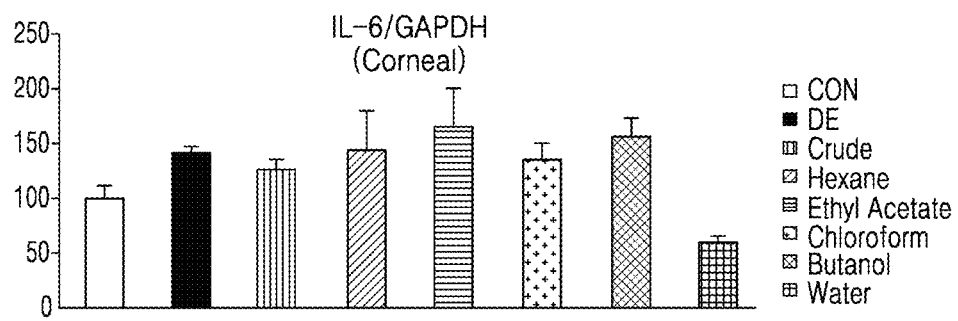
Figure 10D:
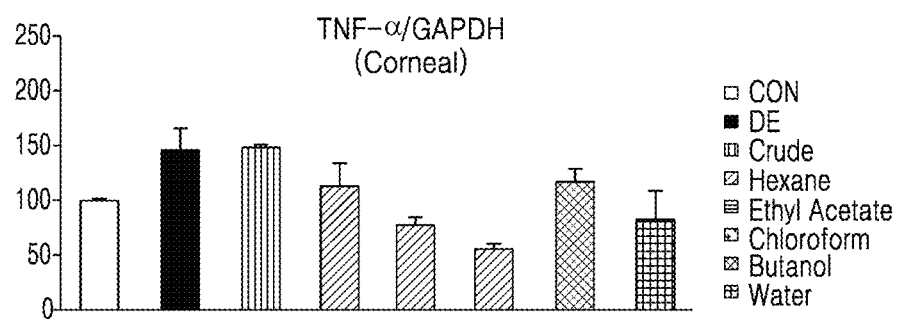
Figure 11A:
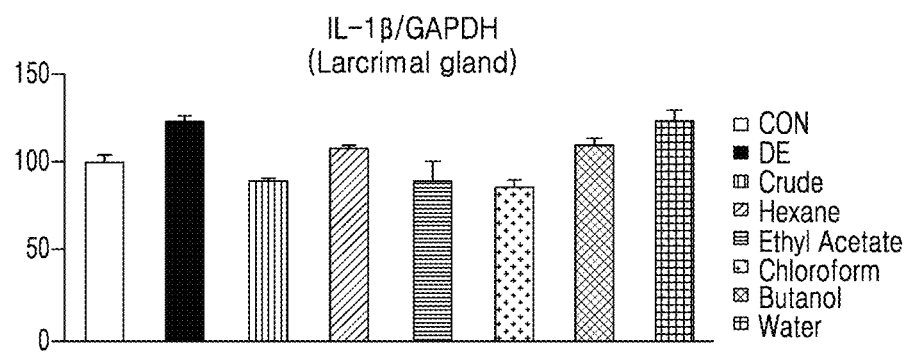
FIGS. 11A, 11B, 11C, and 11D are graphs illustrating expression of inflammatory cytokines in lacrimal glands of mice according to administration of fractions of *Terminalia* fruit (*: $p<0.05$ vs. Con; #: $p<0.05$ vs. DE).
Figure 11B:
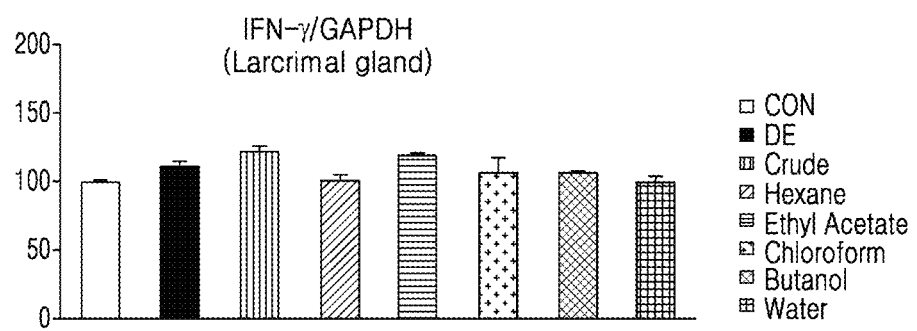
Figure 11C:
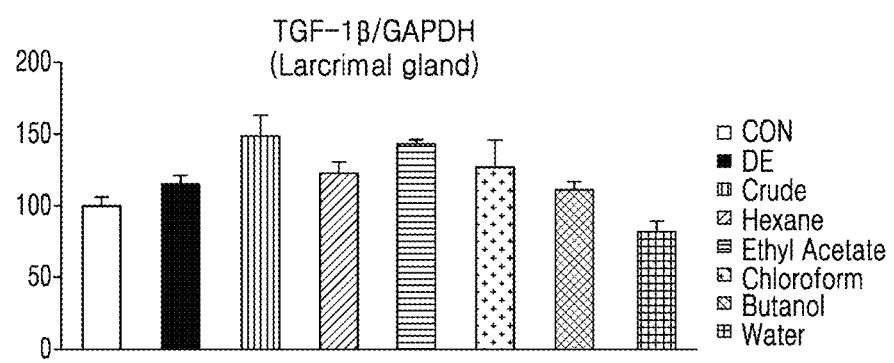
Figure 11D:
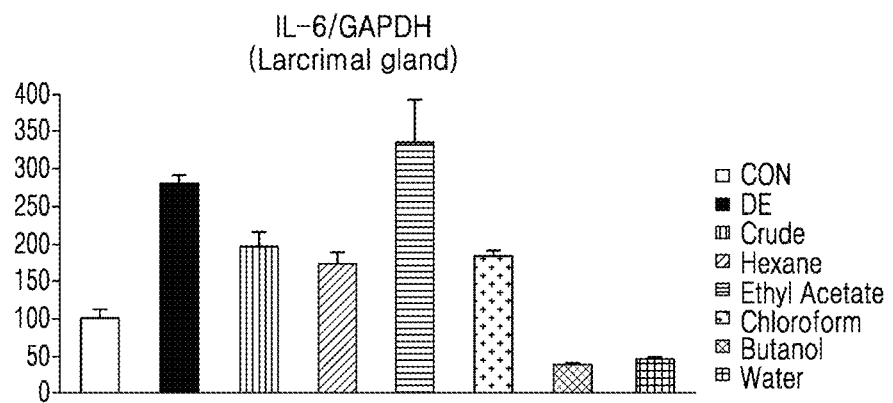

FIG. 9 shows photographs showing morphological changes of lacrimal glands in mice according to administration of hexane fractions of *Terminalia* fruit. As shown in FIG. 9, the number of inflammatory cells around the lacrimal glands of the groups treated with the hexane fractions was reduced, compared to the dry eye syndrome-induced group.

5. Measurement of Expression Level of Inflammatory Cytokine in Cornea and Lacrimal Gland The effects of the fractions of *Terminalia* fruit on expression of cytokines in the corneas and lacrimal glands in the dry eye syndrome induced by the dehumidifier were identified. Particularly, expression levels of mRNA of IL-1β, IFN-γ, TNF-α, and IL-6, which are representative inflammatory cytokines, were measured by qPCR using the animal test design prepared in section 2 above at 14 days after administering the drug. In this case, primer sets of SEQ ID NOS: 1 and 2; SEQ ID NOS: 3 and 4; SEQ ID NOS: 5 and 6; SEQ ID NOS: 7 and 8; SEQ ID NOS: 9 and 10; and SEQ ID NOS: 11 and 12 were used, respectively.

FIGS. 10A, 10B, 10C, and 10D are graphs illustrating expression of inflammatory cytokines in corneas of mice according to administration of fractions of *Terminalia* fruit (*: $p<0.05$ vs. Con; #: $p<0.05$ vs. DE). The inflammatory cytokines measured in FIGS. 10A, 10B, 10C, and 10D were IFN-γ, TNF-α, and IL-6, respectively. As shown in FIGS. 10A, 10B, 10C, and 10D, most of the crude group, the hexane group, the ethylacetate group, the chloroform group, the butanol group, and the water group exhibited increased expression levels of mRNA of the inflammatory cytokines, compared to that of the DE group.

FIGS. 11A, 11B, 11C, and 11D are graphs illustrating expression of inflammatory cytokines in lacrimal glands of mice according to administration of fractions of *Terminalia* fruit (*: $p<0.05$ vs. Con; #: $p<0.05$ vs. DE). In FIGS. FIGS. 10A, 10B, 10C, 10D, 11A, 11B, 110, and 11D, units of the vertical axes are percentage relative to the control group.

The pharmaceutical composition according to an embodiment may be used to prevent or treat dry eye syndrome. That is, the composition may significantly inhibit decreases in amounts of tear secretion, thickness changes and inflammatory responses in corneas, and morphological changes and inflammatory responses in lacrimal glands.

By the method of treating dry eye syndrome according to another embodiment, dry eye syndrome may be efficiently treated.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

The invention claimed is:

1. A method of treating dry eye syndrome in an individual, the method comprising:
   administering a pharmaceutical composition to the individual in an amount effective to treat dry eye syndrome,
   wherein the pharmaceutical composition comprises an extract of *Terminalia chebula* or a fraction thereof as an active ingredient for increasing an amount of tear secretion,
   wherein the extract is obtained using a C1-C6 alcohol, or a mixture of the C1-C6 alcohol, as a solvent,
   wherein the composition comprises the extract of *Terminalia chebula* or a fraction thereof as a single active ingredient, and
   wherein the composition is formulated for oral administration.

2. The method of treating dry eye syndrome in an individual according to claim 1,
   wherein the alcohol is methanol, ethanol, propanol, butanol, pentanol, or hexanol.

3. The method of treating dry eye syndrome in an individual according to claim 1,
   wherein the fraction is a hexane fraction, an ethyl acetate fraction, a butanol fraction, or a water fraction of the extract of *Terminalia chebula*.

4. The method of treating dry eye syndrome in an individual according to claim 1,
   wherein the composition increases an amount of tear secretion or inhibits morphological change in a cornea.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
```

```
<223> OTHER INFORMATION: Synthetic: primer

<400> SEQUENCE: 1
caggcaggca gtatcactca                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic: primer

<400> SEQUENCE: 2
aggccacagg tattttgtcg                                               20

<210> SEQ ID NO 3
<211> LENGTH: 21
<212> TYPE: DNA
<213> ORGANISM: Artificial Sequence
<220> FEATURE:
<223> OTHER INFORMATION: Synthetic: primer

<400> SEQUENCE: 3
atggatgcta ccaaactgga t                                             21

<210> SEQ ID NO 4
<211> LENGTH: 21
<212> TYPE: DNA
<213> ORGANISM: Artificial Sequence
<220> FEATURE:
<223> OTHER INFORMATION: Synthetic: primer

<400> SEQUENCE: 4
tgaaggactc tggctttgtc t                                             21

<210> SEQ ID NO 5
<211> LENGTH: 25
<212> TYPE: DNA
<213> ORGANISM: Artificial Sequence
<220> FEATURE:
<223> OTHER INFORMATION: Synthetic: primer

<400> SEQUENCE: 5
ggaactcttt tcttaggcat tttga                                         25

<210> SEQ ID NO 6
<211> LENGTH: 23
<212> TYPE: DNA
<213> ORGANISM: Artificial Sequence
<220> FEATURE:
<223> OTHER INFORMATION: Synthetic: primer

<400> SEQUENCE: 6
gatggtctcc acactctttt gga                                           23

<210> SEQ ID NO 7
<211> LENGTH: 24
<212> TYPE: DNA
<213> ORGANISM: Artificial Sequence
<220> FEATURE:
<223> OTHER INFORMATION: Synthetic: primer

<400> SEQUENCE: 7
ttgttaccaa ctgggacgac atgg                                          24
```

```
<210> SEQ ID NO 8
<211> LENGTH: 24
<212> TYPE: DNA
<213> ORGANISM: Artificial Sequence
<220> FEATURE:
<223> OTHER INFORMATION: Synthetic: primer

<400> SEQUENCE: 8
gatcttgatc ttcatggtgc tagg                                              24

<210> SEQ ID NO 9
<211> LENGTH: 20
<212> TYPE: DNA
<213> ORGANISM: Artificial Sequence
<220> FEATURE:
<223> OTHER INFORMATION: Synthetic: primer

<400> SEQUENCE: 9
gtcactggag ttgtacggca                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic: primer

<400> SEQUENCE: 10
agccctgtat tccgtctcct                                                   20

<210> SEQ ID NO 11
<211> LENGTH: 21
<212> TYPE: DNA
<213> ORGANISM: Artificial Sequence
<220> FEATURE:
<223> OTHER INFORMATION: Synthetic: primer

<400> SEQUENCE: 11
gccaaggtca tccatgacaa c                                                 21

<210> SEQ ID NO 12
<211> LENGTH: 21
<212> TYPE: DNA
<213> ORGANISM: Artificial Sequence
<220> FEATURE:
<223> OTHER INFORMATION: Synthetic: primer

<400> SEQUENCE: 12
gtccaccacc ctgttgctgt a                                                 21
```